(12) United States Patent
Lima et al.

(10) Patent No.: US 7,910,364 B2
(45) Date of Patent: *Mar. 22, 2011

(54) RAPIDLY CLEAVABLE SUMO FUSION PROTEIN EXPRESSION SYSTEM FOR DIFFICULT TO EXPRESS PROTEINS

(75) Inventors: Christopher D. Lima, New York, NY (US); Elena Mossessova, New York, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 114 days.

This patent is subject to a terminal disclaimer.

(21) Appl. No.: 12/249,334

(22) Filed: Oct. 10, 2008

(65) Prior Publication Data

US 2009/0317868 A1 Dec. 24, 2009

Related U.S. Application Data

(60) Continuation of application No. 10/949,685, filed on Sep. 24, 2004, now Pat. No. 7,498,165, which is a division of application No. 10/188,343, filed on Jul. 2, 2002, now Pat. No. 6,872,551.

(51) Int. Cl.
*C12N 15/00* (2006.01)
*C12N 5/00* (2006.01)
*C12P 21/06* (2006.01)
*C07H 21/00* (2006.01)

(52) U.S. Cl. .................. 435/320.1; 435/69.1; 435/252.1; 435/325; 536/23.1; 536/23.4

(58) Field of Classification Search ........................ None
See application file for complete search history.

(56) References Cited

U.S. PATENT DOCUMENTS

| | | | |
|---|---|---|---|
| 5,643,758 A | 7/1997 | Guan et al. | |
| 6,872,551 B2 * | 3/2005 | Lima et al. | 435/69.7 |
| 7,060,461 B2 | 6/2006 | Butt et al. | |
| 7,498,165 B2 * | 3/2009 | Lima et al. | 435/320.1 |

OTHER PUBLICATIONS

Yoshinobu Ichimura, Takayoshi Kirisako, Toshifumi Takao, Yoshinori Satomi, Yasutsugu Shimonishi, Naotada Ishihara, Noboru Mizushima, Isei Tanida, Eiki Kominami, Mariko Ohsumi, Takeshi Noda and Yoshinori Ohsumi, "A ubiquitin-like system mediates protein lipidation", Nature (2000) 408: 488-492.
Elena Mossessova and Christopher D. Lima, "Ulp1-SUMO Crystal Structure and Genetic Analysis Reveal Conserved Interactions and a Regulatory Element Essential for Cell Growth in Yeast", Molecular Cell (2000) 5: 865-876.
Edward T.H. Yeh, Limin Gong, Tetsu Kamitani, "Ubiquitin-like proteins: new wines in new bottles", Gene (2000) 248: 1-14.
Shyr-Jiann Li and Mark Hochstrasser, "The Yeast ULP2 (SMT4) Gene Encodes a Novel Protease Specific for the Ubiquitin-Like Smt3 Protein", Molecular and Cellular Biology (2000) 20: 2367-2377.
Katsunori Tanaka, Junko Nishide, Koei Okazaki, Hiroaki Kato, Osami Niwa, Tsuyoshi Nakagawa, Hideyuki Matsuda, Makoto Kawamukai, and Yota Murakami, "Characterization of a Fission Yeast SUMO-1 Homologue, Pmt3p, Required for Multiple Nuclear Events, Including the Control of Telomere Length and Chromosome Segregation", Molecular and Cellular Biology (1999) 19: 8660-8672.
Shyr-Jiann Li and Mark Hochstrasser, "A new protease required for cell-cycle progression in yeast", Nature (1999) 398: 246-251.
David P. Lane and Peter A. Hall, "SUMO-1: wrestling with a new ubiquitin-related modifier", TIBS (1997) 22:374-376.
Erica S. Johnson, Ingrid Schwienhorst, R. Jürgen Dohmen, and Günter Blobel, "The ubiquitin-like protein Smt3p is activated for conjugation to other proteins by an Aos1p/Uba2p heterodimer", The EMBO Journal (1997) 16: 5509-5519.
Kohno et al., "A new general method for the biosynthesis of stable isotope-enriched peptides using a decahistidine-tagged ubiquitin fusion system: An application to the production of mastoparan-X uniformly enriched with 15N and 15N/13C", (Journal of Biomolecular NMR, 1998, 12:109-121).
Wang et al., "Biotin-Ubiquitin Tagging of Mammalian Proteins in *Escherichia coli*", Protein Expression and Purification, 30:140-149 (2003).
Yaseen et al., "Two Distinct Classes of Ran-Binding Sites on the Nucleoporin Nup-358", Proc. Natl. Acad. Sci, vol. 96, p. 5516-5521 (1999).
Stanton et al., "Analysis of the Human Herpervirus-6 Immediate-Early 1 Protein", Journal of General Virology, 83, p. 2811-2820 (2002).
Muller et al., "Conjugation with the Ubiquitin-Related Modifier SUMO-1 Regulates the Partitioning of PML Within the Nucleus", The EMBO Journal, vol. 17, No. 1, p. 61-70 (1998).
Poukka, et al., "Ubc9 Interacts with the Androgen Receptor and Activates Receptor-Dependent Transcription", Journal of Biological Chemistry, vol. 274, No. 27, p. 19441-19446 (1999).
Champion pET SUMO Protein Expression System (Invitrogen Instruction Manual) Version A Jan. 27, 2004.
Melchior, F., "SUMO-Nonclassical Ubiquitin", Annu. Rev. Cell Dev. Biol., 16:591-626 (2000). Chosed et al., "Evolution of a Signalling System that Incorporates both Redundancy and Diversity: *Arabidopsis* SUMOylation", Biochem J. 398, 521-529 (2006).

(Continued)

*Primary Examiner* — Anand U Desai
(74) *Attorney, Agent, or Firm* — Hoffmann & Baron, LLP (57) ABSTRACT

A recombinant expression system for the expression of a poly amino acid, peptide or protein is provided. The poly amino acid of interest is expressed as a fusion protein that includes an amino acid sequence recognized and cleaved by a Ulp1 protease. The amino acid sequence joined to the poly amino acid of interest is preferably from a SUMO (small ubiquitin-like molecule) protein. This sequence imparts favorable solubility and refolding properties to the fusion protein. A purification tag may also be incorporated into the fusion protein for ease of isolation. This recombinant expression system is particularly advantageous for expression and rapid and highly specific cleavage and purification of poly amino acids that have low solubilities or are difficult to express in other systems.

31 Claims, 5 Drawing Sheets

OTHER PUBLICATIONS

Hannig, et al., "Strategies for Optimizing Heterologous Protein Expression in *Escherichia coli*", Trends in Biotechnol., 16:54-60 (1998).

Rosenfeld, S., "Use of *Pichia pastoris* for Expression of Recombinant Proteins", Methods in Enzymology, 306:154-169 (1999).

Product Catalog by LifeSensor, Inc. entitled "SUMOpro® -3 Expression Vector" (2006).

Cookson, "Pathways to Parkinsonism", Neuron, vol. 37, 7-10 (2003).

Hockstrasser, "Evolution and Function of Ubiquitin-Like Protein-Conjugation Systems", Nature Cell Biology, vol. 2 p. E153-E157(2000).

Johnson et al., "Cell Cycle-Regulated Attachment of the Ubiquitin-Related Protein SUMO to the Yeast Septins", Journal of Cell Biology, vol. 147, No. 5, p. 981-993 (1999).

Li et al., "The Yeast ULP2 (SMT4) Gene Encodes a Novel Protese Specific for the Ubiquitin-Like Smt3 Protein", Molecular and Cellular Biology, vol. 20, No. 7, p. 2367-2377 (2000).

Li et al., "The Ulp1 SUMO Isopeptidase: Distinct Domains Required for Viability, Nuclear Envelope Localization, and Substrate Specificity", Journal of Cell Biology, vol. 160, No. 7, p. 1069-1-81 (2003).

Matunis, et al., "A Novel Ubiquitin-Like Modification Modulates the Partitioning of the Ran-GTPhase-Activating protein Ran GAP1 Between the Cytosol and the Nuclear Pore Complex", Journal of Cell Biology, vol. 135, No. 6, Pt. 1, p. 1457-1470 (1996).

Guzzo et al., "Systematic Analysis of Fusion and Affinity Tags Using Human Aspartyl-tRNA Synthetase Expressed in *E. coli*", Protein Expression and Purification 54, p. 166-175 (2007).

Rao-Naik et al., "The Rub Family of Ubiquitin-Like Proteins", Journal of Biological Chemistry, vol. 273, No. 52, p. 34976-34982 (1998).

Reverter, et al., "A Basis for SUMO Protease Specificity Provided by Analysis of Human Senp2 and a Senp2-SUMO Complex", Structure, vol. 12, p. 1519-1531 (2004).

Schwartz et al., "A Superfamily of Protein Tags: Ubiquitin, SUMO and Related Modifiers", Trends in Biochemical Sciences, vol. 28, No. 6, p. 321-328 (2003).

Shi et al., "Association of FHIT (Fragile Histidine Triad), a Candidate Tumour Suppressor Gene, with the Ubiquitin-Conjugating Enzyme hUBC9", Biochem J., 352, 443-448 (2000).

Weeks, et al., Ligation Independent Cloning Vectors for Expression of SUMO Fusions, Protein Expression and Purification 53, 40-50 (2007).

\* cited by examiner

Figure 1A.

| Promoter | StartCodon | 6-10-polyhis tag | Smt3 (N•13 or native) | MCS | Stop |
|---|---|---|---|---|---|
| | | | | Ulp1(403-621)p cleavage site | |
| (T7 or any) | Met----------------------HHHHHHHHHH-------Smt3----------------------------GlyGlySer----------------------------Stop |
| | ATG--------------------------------------------------------------------------------------------GGATCC--------------------------TAA |
| | | | | BamHI | |

RAPIDLY CLEAVABLE SUMO FUSION PROTEIN EXPRESSION SYSTEM FOR DIFFICULT TO EXPRESS PROTEINS

CROSS-REFERENCE

This application is a continuation of U.S. application Ser. No. 10/949,685 filed on Sep. 24, 2004, issued on Mar. 3, 2009 as U.S. Pat. No. 7,498,165, which is a divisional application of U.S. application Ser. No. 10/188,343 filed on Jul. 2, 2002, issued on Mar. 29, 2005 as U.S. Pat. No. 6,872,551, which claims the benefit of PCT/US02/14062 filed May 6, 2002, which claims the benefit of U.S. Provisional Application Ser. No. 60/329,080 filed on Oct. 12, 2001, which claims the benefit of U.S. Provisional Application Ser. No. 60/288,656 filed on May 4, 2001. The specifications of U.S. application Ser. Nos. 10/949,685; 10/188,343; 60/329,080; 60/288,656 and International Application No. PCT/US02/14062 are hereby incorporated by reference in their entirety.

BACKGROUND

Numerous recombinant expression systems are available for production of foreign proteins. See for example Ausubel et al. (Eds.), Current Protocols in Molecular Biology, Wiley, NY (1999); Wu, R. (Ed.), Recombinant DNA methodology TI, Academic Press, NY (1995). One problem common to the available expression systems is that it is difficult to efficiently express many foreign proteins in active form at high levels. Another difficulty arises when the expression of the protein of interest leads to precipitation of the protein as an insoluble amorphous mass in the host cell bearing the expression vector. There remains a need for an efficient expression system, especially for proteins that are difficult to express. Optimally, the expression system should provide high levels of soluble, correctly folded, or active recombinant peptides or proteins that may be easily purified from the expression system.

SUMMARY OF THE INVENTION

The present invention provides a recombinant fusion protein that comprises an expression enhancing amino acid sequence cleavable by Ulp1 protease or an active fragment of Ulp1 protease (for example the fragment from amino acid positions 403 to 621) and a recombinant poly-amino acid of interest, particularly one that is difficult to express in a recombinant expression system. The fusion protein may also include a purification tag for ease of isolation.

The invention further provides a method of expressing a recombinant poly-amino acid of interest that is difficult to express in a recombinant expression system, by the steps of providing a vector encoding a fusion protein that includes the recombinant poly-amino acid of interest, preferably located C-terminally to a purification tag. The purification tag and the recombinant poly-amino acid of interest are separated by an expression enhancing amino acid sequence cleavable by Ulp1 protease or an active fragment of Ulp1 protease, such as the fragment from the amino acid residue at position 403 to the amino acid residue at position 621. The fusion protein is expressed from the vector in a suitable recombinant host cell.

The invention also provides a method for purifying a poly-amino acid of interest by providing a vector encoding a recombinant fusion protein that comprises an expression enhancing amino acid sequence cleavable by Ulp1 protease or an active fragment of the Ulp1 protease (for example the fragment from amino acid position 403 to 621) and the recombinant poly-amino acid of interest; expressing the fusion protein from the vector in a suitable recombinant host cell; and purifying the fusion protein by means of the purification tag and cleaving the purified fusion protein with a Ulp1 protease or Ulp1 protease fragment.

Also provided are expression vectors encoding the recombinant fusion proteins that comprise an expression enhancing amino acid sequence cleavable by Ulp1 protease or an active fragment of Ulp1 protease (for example the fragment from amino acid position 403 to 621) and a recombinant poly-amino acid of interest expressed from an efficient promoter.

In another embodiment of the present invention, host cells carrying the expression vectors encoding recombinant fusion proteins that include an expression enhancing amino acid sequence cleavable by Ulp1 protease or an active fragment of Ulp1 protease (for example the fragment from amino acid position 403 to 621) and a recombinant poly-amino acid of interest are provided.

Also provided are kits and products comprising: a recombinant vector encoding a fusion protein comprising a purification tag, an expression enhancing amino acid sequence cleavable by Ulp1 protease or an active fragment of Ulp1 protease (for example the fragment from amino acid position 403 to 621) and a multiple cloning site suitable for cloning a nucleic acid sequence encoding a poly-amino acid of interest, wherein the poly-amino acid of interest is difficult to express in a recombinant system; and further comprising a Ulp1 protease preparation. The kit may further comprise an antibody specific for the expression enhancing amino acid sequence cleavable by Ulp1 protease or an active fragment of Ulp1 protease (for example the fragment from amino acid position 403 to 621).

In yet another embodiment, the present invention provides an active fragment of the Ulp1 protease. Preferably, the active fragment of the Ulp1 protease comprises amino acid residues 403-621 of Ulp1. More preferably still, the active fragment of the Ulp1 protease consists essentially of amino acid residues 403-621 of Ulp1.

The present invention yet further provides nucleic acid molecules, including DNA and RNA molecules that include a nucleotide sequence encoding an expression enhancing amino acid sequence cleavable by Ulp1 protease or an active fragment of Ulp1 protease. The nucleic acid sequence encoding the expression enhancing amino acid sequence cleavable by Ulp1 protease or an active fragment of Ulp1 protease may also encompasses a restriction enzyme recognition site downstream of the nucleotide sequence encoding the expression enhancing amino acid sequence cleavable by Ulp1 protease or Ulp1 protease fragment. The restriction enzyme recognition site included in the nucleic acid molecule being suitable for cloning a nucleotide sequence encoding a poly-amino acid of interest. The nucleic acid molecules of the invention are particularly useful for the expression and purification of poly-amino acid of interest that are difficult to express in recombinant expression systems.

BRIEF DESCRIPTION OF THE FIGURES

The fusion protein includes a poly amino acid of interest, the Smt3 fragment containing the Ulp1 cleavage site and a polyhistidine tag (SEQ. ID. NO: 1) expressed from a strong promoter of an expression vector encoding the fusion protein.

Peak 1 in the HPLC trace corresponds to the sample of lane 2 in the SDS-PAGE gel shown in FIG. 2. Peak 2 in the HPLC trace corresponds to the sample of lanes 3 and 4 in the SDS- PAGE gel of FIG. 2. Peak 3 in the HPLC trace corresponds to the sample of lane 5 in the SDS-PAGE gel of FIG. 2. Peak 4 in the HPLC trace corresponds to the sample of lane 6 in the SDS-PAGE gel of FIG. 2.

Lane 1 contains the mixture that was loaded onto the column. Lanes 2, 3, and 4 contain non-protein absorbing material. Lane 5 contains the IκBα peptide. Lane 6 contains Smt3.

Lanes 1-4: N-terminally Smt3 tagged *E. coli* PSS. Lane 1: Induced culture. Lane 2: Lysed culture. Lane 3: Detergent-soluble fraction. Lane 4: Purified Ni-affinity fraction. Lanes 5-8: C-terminal histidine tagged *E. coli* PSS. Lane 5: Induced culture. Lane 6: Lysed culture. Lane 7: Detergent-soluble fraction. Lane 8: Purified Ni-affinity fraction. Lanes 9-12: N-terminal Smt3 tagged *S. cerevisiae* PSS. Lane 9: Induced culture. Lane 10: Lysed culture. Lane 11: Detergent-soluble fraction. Lane 12: Purified Ni-affinity fraction. Lane 13: Molecular weight standards.

The high molecular weight bands evident in lanes 4 and 12 represent recombinant Smt3-PSS enzymes. Some degradation of the Smt3 fusion is evident in lane 12.

Lane 1: Smt3-fusion. Lane 2: Smt3 and fusion partner, post-cleavage. Lane 3: Smt3-fusion. Lane 4: Thrombin cleavage. Lane 5: Smt3. Lane 6: Molecular weight standards.

Lane 1: Molecular weight standards. Lane 2: mt3 and capping enzyme, post-cleavage. Lane 3: Smt3-capping enzyme fusion. Lane 4: Smt3 and capping enzyme, post-cleavage.

Lanes 1-3: Fractions of Ni-purified Smt3-IκBα fusion protein. Lanes 4-5: Smt3 and IκBα, post-cleavage. Lanes 6-7: Lower loading of samples of lanes 4-5.

DETAILED DESCRIPTION OF THE INVENTION

The present invention provides recombinant fusion proteins incorporating a poly amino acid of interest and an expression enhancing amino acid sequence that includes a Ulp1 protease cleavable cleavage site. The Ulp1 protease cleavable site may be any Ulp1 cleavable site, such as for example a Ulp1 protease cleavable site from a ubiquitin-like protein e.g. a SUMO (small ubiquitin-like molecule). The SUMO may be, for instance, Smt3 from yeast, or a fragment of Smt3 that retains the ability to be recognized and cleaved by Ulp1. Examples of such a fragment of Smt3 include the fragment from amino acid positions 14-98 of Smt3 and the fragment from amino acid positions 1-98 of Smt3.

The Smt3 amino acid sequence may be deduced from the SMT3 gene sequence found at nucleotide positions 1,469,403-1,469,708 of Chromosome IV of *Saccharomyces cerevisiae*. (NCBI database at www.ncbi.nlm.nih.gov/entrez/query.fcgi). Both the genomic sequence (SEQ. ID. NO: 2) and the deduced amino acid sequence (SEQ. ID. NO: 3) are shown below:

SMT3 Genomic Sequence from *S. cerevisiae*

```
1469403
atgtcgga ctcagaagtc aatcaagaag ctaagccaga ggtcaagcca gaagtcaagc 1469461
ctgagactca catcaattta aaggtgtccg atggatcttc agagatcttc ttcaagatca 1469521
aaaagaccac tcctttaaga aggctgatgg aagcgttcgc taaaagacag ggtaaggaaa 1469581
tggactcctt aagattcttg tacgacggta ttagaattca agctgatcag acccctgaag 1469641
atttggacat ggaggataac gatattattg aggctcacag agaacagatt ggtggtgcta 1469701
cgtattag
```

Smt3p Amino Acid Sequence

The *Saccharomyces cerevisiae* Smt3p 101 amino acid sequence deduced from the SMT3 genomic sequence is as follows:

```
  1 MSDSEVNQEA KPEVKPEVKP ETHINLKVSD GSSEIFFKIK KTTPLRRLME      50
 60 AFAKRQGKEM DSLRFLYDGI RIQADQTPED LDMEDNDIIE AHREQIGGAT Y    101
```

The fusion protein incorporates the peptide or protein of interest, which is hereinafter interchangeably referred to as a poly-amino acid. The poly-amino acid may be a peptide or a protein that is difficult to express in a recombinant expression system. The poly amino acid of interest may be conveniently released from the fusion protein by cleavage with a Ulp1 protease or an active fragment of the Ulp1 protease. In a preferred embodiment, the active fragment of the Ulp1 protease is a fragment of Ulp1 protease capable of a rapid and specific cleavage of the Ulp1 cleavage site. Optimally the Ulp1 protease fragment is Ulp1 (403-621).

Preferably, the poly-amino acid is known to be difficult to express in a recombinant expression system. The polyamino acid may be of any size, including for example, a short peptide from about 6 amino acids, preferably from about 10 amino acids, to an average size protein of about 300 amino acids in length, or even a large protein of greater than about 600 amino acids in length. Large proteins of over 1000 amino acids in length are often difficult to express at high levels in recombinant systems.

For the purposes of the present specification, poly-amino acids that are difficult to express in a recombinant system are those peptides and proteins that when expressed in a heretofore known recombinant expression system are inefficiently or defectively expressed, or both. Poly-amino acids that are difficult to express in recombinant systems are well known. Examples of difficult to express poly-amino acids include for instance, membrane associated proteins, proteins and peptides that precipitate in recombinant host cells, and those that are produced in non-native or inactive forms.

For purposes of the present application, inefficient expression means low level expression of the poly-amino acid. This may occur for any of a number of causes, including for instance any one or more of the following: poor efficiency of expression of the coding messenger, mRNA from the promoter driving expression; poor stability of the mRNA; poor translation efficiency of the mRNA; and poor stability of the expressed translation product. The expression of the poly-amino acid may also be toxic to the host cell in which it is expressed. Such toxicity may be due any of a number of reasons, including for instance defective processing or defective transport across membranes, each of which may cause build up of the recombinant protein or peptide, in a particular compartment or cellular structure, which may cause growth inhibition or may be toxic to the cell.

For the purposes of the present specification, inefficiently expressed poly-amino acids means those proteins or peptides that are expressed at 1% or less than 1% of total protein by weight in recombinant expression systems that efficiently express other peptides or proteins. Efficient expression includes expression of ten percent or more of the total cell protein.

Difficult to express poly-amino acids include those that are defective in structure or function when expressed in a recombinant system. Examples of defective expression of a poly-amino acid include, for example, expression of insoluble, amorphous, crystalline, inactive or incorrectly folded peptides or proteins.

Examples of difficult to express poly-amino acids include immunoglobulin chains. Functional antibodies have been assembled from recombinant immunoglobulin chains, see for example, Cabilly et al. Generation of antibody activity from immunoglobulin polypeptide chains produced in *Escherichia coli*. Proc. Natl. Acad. Sci. U.S.A. (1984) 81(11):3273-7 and Skerra and Pluckthun, Assembly of a functional immunoglobulin Fv fragment in *Escherichia coli*. Science (1988) 240: 1038-41.

Fusion proteins of immunoglobulin functional domains have also been expressed in *E. coli* and used as mutagenesis targets. See for example, Kolmar et al. General mutagenesis/gene expression procedure for the construction of variant immunoglobulin domains in *Escherichia coli*. Production of Bence-Jones protein REIv via fusion to β-lactamase. J. Mol. Biol. (1992) 228(2):359-65. More recently single chain antibodies and antibody fragments have been expressed in *E. coli*. See for example, Zhou et al. Cloning and expression in *Escherichia coli* of a human gelatinase B-inhibitory single chain immunoglobulin variable fragment (scFv). (1997) FEBS Lett. 414(3): 562-6.

The present expression system provides higher levels of expression. The SUMO or SUMO fragment stabilizes the poly-amino acid of interest and enhances the solubility of the expressed fusion protein, enabling correct refolding and conferring monomeric expression without any toxic effects on the host cell.

The SUMO may be any small ubiquitin-like molecule that includes a Ulp1 cleavable site. Preferably the small ubiquitin-like molecule that includes a Ulp1 cleavable site is the Smt3 protein of yeast, or more preferably a fragment of the Smt3 protein, such as the protein encoded by the amino acid sequence of Smt3 from residues 13-101, or most preferably, the protein encoded by the amino acid sequence of Smt3 from 1-98. The Ulp1 protease and active fragments of the Ulp1 protease cleave site Smt3 at the sequence—Gly-Gly-Ser between the Gly and Ser residues. By use of an N-terminal deletion of Smt3 the inventor has shown that a fragment of Smt3 comprising residues 14-98 is sufficient for Ulp1 recognition. More extensive deletions of Smt3, cause loss of the Smt3 protein fold, and thus cause loss of the ability to be recognized and cleaved when present in Smt3 fusions.

In the proteins of the present invention, poly-amino acids may be joined to amino acid sequences as an N-terminal or a C-terminal fusion. Preferably, the fusion is a C-terminal fusion with the expression enhancing amino acid sequence cleavable by Ulp1(403-621) preferably at the N-terminus. The fusion protein may further include a purification tag for ease of purification. The purification tag may be any purification tag for which a cognate binding agent or antibody is available. An example of a preferred purification tag for which a cognate binding agent is readily available is the poly-histidine tag. The cognate binding agent for the poly-histidine tag is a metal affinity column such as a nickel-affinity column. Other useful purification tags include any epitope tag for which a cognate high affinity antibody is available or can be raised by well known methods. Examples of such common purification tags include glutathione S-transferase (GST), an epitope of GST, thioredoxin, or an epitope of thioredoxin and the commercially available FLAG epitope of influenza virus HA antigen. The resulting tagged recombinant polypeptide can be purified by standard means, such as the existing Ni-affinity chromatography for purification of poly-histidine tagged proteins.

Any protease capable of cleaving a Ulp1 cleavage site of the fusion protein bearing a Ulp1 cleavable, or Ulp1(403-621) cleavable site may be used to specifically cleave and liberate the tagged expression enhancing moiety from the recombinant polyamino acid of interest after purification. Examples of suitable proteases include Ulp1 protease, an active fragment of Ulp1 protease, or in a preferred embodiment, a fragment of the Ulp1 protease, such as the fragment including the amino acid residues 403-621 of Ulp1. Optimally, the fragment of the Ulp1 protease including the amino acid residues 403-621 of Ulp1 is the Ulp1 (403-623) fragment. The cleavage of recombinant polypeptide by Ulp1 or active fragments of Ulp1 is analogous to the processing of full-length SUMO to its mature form in yeast.

Cleavage of fusion proteins that include a Ulp1 cleavage site is rapid and highly specific. This cleavage reaction may be efficiently carried out under conditions that would inhibit many other site-specific proteases. For example, the fusion proteins may be cleaved at 4° C. under standard conditions of buffer, ionic strength and fusion protein and concentration of a Ulp1 fragment, such as for example the Ulp1(403-621) fragment.

The invention also provides nucleic acid molecules and expression vectors encoding the recombinant fusion proteins described above. The nucleic acid molecules of the present invention include DNA and RNA molecules having a nucleotide sequence encoding an expression enhancing amino acid sequence cleavable by Ulp1 protease or an active fragment of Ulp1 protease. The nucleic acid may be natural in origin, or may be synthetic. Semi-synthetic nucleic acid molecules comprising both synthetic and natural components are contemplated in the present invention. Semi-synthesis is particularly useful for the introduction of unique restriction sites and sequences encoding protease cleavage sites or specific epitopes etc.

The expression vector may be any expression vector selected from the many expression vectors known in the art. Preferably, the expression vector is a bacterial expression vector. The vector comprises a strong promoter, a sequence encoding a purification tag and at least one cloning site, or a multiple cloning site for cloning of a poly amino acid-encoding fragment in-frame with the encoded Ulp1-cleavable amino acid sequence. The promoter may be any strong promoter. Preferably, the strong promoter is a constitutive or a regulatable promoter. Suitable promoters are well known in the art. Some examples include any one of the T7, trc, lac and tac promoters. A preferred vector incorporating a strong promoter is pET28b, commercially available from Novagen (Madison, Wis.).

The purification tag may be any purification tag, or affinity tag, such as glutathione-S-transferase (GST), polyhistidine, polyarginine, the FLAG™ epitope, streptavidin, maltose binding protein, thioredoxin, and intein or any epitope recognized by a high affinity antibody available for purification. (Examples of these and other tags and useful purification techniques as well as many general methods for protein expression and purification are found in Sambrook and Russel, 2001. Molecular Cloning, A Laboratory Manual. Third Edition. Cold Spring Harbor laboratory, Cold Spring Harbor Press, NY).

U.S. Pat. No. 4,851,341 discloses a process for purifying a recombinant fusion protein having an N-terminal sequence comprising multiple anionic amino acid residues. The process includes forming a complex of the protein with a divalent cation dependent monoclonal antibody specific for the sequence, isolating the complex, and dissociating antibody and protein by selectively depleting the concentration of divalent cations in contact with the complex. A particular calcium-dependent monoclonal antibody, 4E11, may be used in the process where the peptide DYKDDDDK (SEQ. ID. NO: 4) is incorporated into the fusion protein for identification or purification as its cognate antibody. Such processes and fusion proteins may also be useful in the practice of the present invention.

The multi-cloning site (MCS) preferably includes a BamHI site and the stop codon, although any restriction enzyme site compatible with an in-frame C-terminal cloning strategy is suitable. Large purification tags may be convenient for some applications. These large purification tags include, for example, staphylococcal protein A, (Uhlen et al. 1983. Gene 23: 369); *E. coli* trpE, anthranilate synthetase (Itakura et al. 1977. Science 198: 1056 and bacterial β-galactosidase (Gray et al. 1982. Proc. Natl. Acad. Sci. USA 79: 6598).

The fusion protein may comprise the poly-amino acid of interest and one or more purification tags, epitope tags or the like. The fusion protein may include the poly-amino acid of interest bounded by the site cleavable by Ulp1 or a Ulp1 fragment on one side and by another cleavable site at the other side. Other cleavable sites include sites cleavable by collagenase (Germino & Bastis, 1984. Proc. Natl. Acad. Sci. USA 81:4692); renin (Haffey et al. 1987. DNA 6:565); Factor Xa protease (Nagai & Thogersen, 1984. Nature 309: 810); enterokinase (Prickett et al. 1989. BioTechniques 7:580).

A fusion system which uses chemical cleavage rather than an enzymatic cleavage has also been reported (for a review see, Nilsson, B., Meth. Enz. 198:3 (1991). In this system, staphylococcal protein A forms the amino-terminal portion of the fusion protein facilitating affinity purification on IgG-Sepharose. The vector used to generate the fusion protein contains sequentially (amino to carboxy-terminus) the signal sequence of protein A, two copies of the IgG binding domains of protein A, followed by the peptide or protein of interest. The signal sequence of protein A facilitates the appearance of the fusion protein in the culture medium. After purification, the poly-amino acid of interest is cleaved from the fusion protein by treatment with hydroxylamine, cyanogen bromide or N-chlorosuccinamide. Hydroxylamine cleaves between the sequence Asn-Gly and thus requires that the first amino acid of the poly-amino acid of interest be glycine. Cyanogen bromide cleaves at methionine residues and therefore when the poly-amino acid of interest contains internal methionine residues a partial digestion must be performed. N-chlorosuccinamide cleaves on the carboxy-terminal side of tryptophan residues and therefore the poly-amino acid of interest must not contain tryptophan residues. Thus, the use of protein A fusion system in conjunction with chemical cleavage of the fusion protein is limited. Chemical cleavage requires the absence of specific residues internal to the poly-amino acid of interest or the presence of specific amino acids in the sequence at the junction between the poly-amino acid of interest and the linker sequences.

The practice of the present invention employs conventional molecular biology, microbiology and recombinant DNA techniques that are known in the art. These techniques are well known and fully disclosed in the literature. See for example Sambrook and Russel (Eds). Molecular cloning, A Laboratory Manual, 2001, Cold Spring Harbor Labs, Cold Spring Harbor Press, NY; Oligonucleotide Synthesis, M J Gait, Ed., 1984; Transcription and Translation, Hames & Higgins, 1984.

Figure 1A:
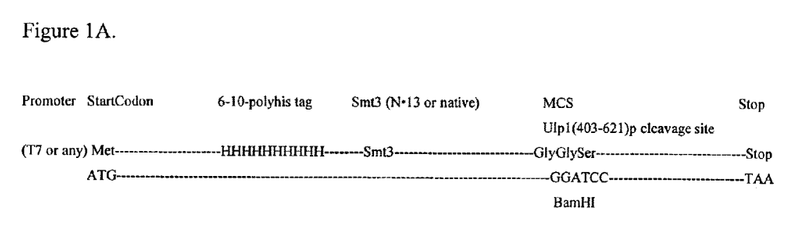
FIG. 1A. Schematic of a Fusion Protein of the Invention.

A schematic of an example of the fusion protein and elements of the vector encoding it are shown in FIG. 1A. The native C-terminal glycine (position 98) of Smt3 overlaps with the coded in-frame glycine of the BamHI site.

The recombinant fusion protein is expressed in a suitable host cell. The host cell may be a prokaryotic host cell or alternatively the host cell may be a eukaryotic host cell. Preferably the suitable host is a prokaryotic host, such as for instance, an *E. coli* cell. Suitable alternative hosts include eukaryotic hosts that have low endogenous Ulp1-like cleavage activities. The combination of recombinant expression vector and suitable host cell is commonly referred to as a recombinant expression system.

In one embodiment the vector preferably comprises a DNA plasmid vector expressing a His-tagged fusion protein of an expression enhancing amino acid sequence of the yeast SUMO, Smt3 fused to a poly-amino acid of interest. An expression and purification system expressing such a recombinant fusion protein has several advantages or features over commercially available systems. These advantages include the following:

1. The Smt3 recombinant fusion protein is monomeric, soluble and highly overexpressed in bacteria. In embodiments including a purification tag, such as a poly-histidine tag (His-tag), the recombinant fusion protein and can be readily purified by standard methods. (For example by Ni-affinity chromatography in the case of His-tagged fusion proteins).
2. The tagged Smt3 portion of the recombinant fusion protein is highly soluble, leading to the increased solubility of poly-amino acids that are insoluble or only partially soluble when expressed alone.

3. The tagged Smt3 portion of the recombinant fusion protein is small, interposing little if any interference to normal folding processes and allowing refolding if the expressed recombinant fusion protein is insoluble.

4. The tagged Smt3 portion of the recombinant protein is short, of the order of a hundred amino acids in length, (118 residues in one embodiment of the His-tagged Smt3 construct) making the percent by mass of the recombinant poly amino acids fused to Smt3 higher than in presently available expression systems.

5. A considerable benefit is derived from the fact that in a tagged Smt3 fusion molecule comprising an N-terminal tag coupled to Smt3 (or an Smt3 fragment) that is in turn coupled to a poly amino acid of interest, the N-terminal tag on the Smt3 is oriented in the opposite direction from the poly amino acid of interest. This ensures that the Ulp1 cleavage site is accessible for cleavage even when the tagged Smt3 fusion molecule is immobilized by binding the purification tag.

6. The Ulp1 fragment, $Ulp1(403-621)_p$ is stable, active, and highly specific for Smt3, resulting in little if any background proteolysis of the recombinant poly amino acid fusion partner. This is of particular interest to systems where the respective fusion partner is susceptible to non-specific proteolysis (ie., unfolded recombinant peptide fusions).

7. Smt3 antibody is available that specifically binds an epitope of Smt3. The antibody binds the Smt3 recombinant fusion proteins that carry this Smt3 epitope and may be used to detect these recombinant fusion proteins even when expressed at low levels.

8. The poly amino acid of interest cleaved from the recombinant fusion protein, if cloned into the BamHI site of pSUMO, located between Smt3 and the fusion partner, contains only one non-native added amino acid (serine) at the N-terminus of the released recombinant poly amino acid product.

9. The expression of Smt3-fusion proteins/peptides in isotopically labeled media will result in samples suitable for NMR studies. This feature is highly desirable due to the prohibitive cost of synthetically derived labeled poly-amino acids.

10. Large amounts of recombinant peptide are obtained from the recombinant host system due in part because of the stability conferred by Smt3 and the precise cleavage of peptide from Smt3 with Ulp1. In one instance of a 15 mer peptide fusion, 5-10 mg of the peptide was produced per liter of bacterial culture.

A nucleic acid cassette for insertion of DNA encoding an ATG translational start site, an Smt3 fragment and a multiple cloning site (mcs) into any recombinant vector system is also provided. This cassette may be inserted into any suitable recombinant vector system to produce a vector for insertion of nucleic acid encoding any poly-amino acid of interest. Suitable recombinant vectors include plasmid vectors and phage vectors. Some suitable prokaryotic cloning vectors include plasmids from E. coli, such as colE1, pCR1, pBR322, pMB9, pUC, pKSM, and RP4. Prokaryotic vectors also include derivatives of phage DNA such as M13 fd, and other filamentous single-stranded DNA phages.

Other suitable vectors for expressing proteins in bacteria, especially E. coli, include the pK233 (or any of the tac family) plasmids, T7, pBluescript II, bacteriophage lamba ZAP, and lambda $P_L$ (Wu, R. (Ed.), Recombinant DNA Methodology II, Methods Enzymol., Academic Press, Inc., New York, (1995)). Examples of vectors that express fusion proteins are PATH vectors described by Dieckmann and Tzagoloff in J. Biol. Chem. 260, 1513-1520 (1985). These vectors contain DNA sequences that encode anthranilate synthetase (TrpE) followed by a polylinker at the carboxy terminus. Other expression vector systems are based on β-galactosidase (pEX); maltose binding protein (pMAL); glutathione S-transferase (pGST or PGEX)—see Smith, D. B. Methods Mol. Cell. Biol. 4:220-229 (1993); Smith, D. B. and Johnson, K. S., Gene 67:31-40 (1988); and Peptide Res. 3:167 (1990), and TRX (thioredoxin) fusion protein (TRXFUS)—see LaVallie, R. et al., Bio/Technology 11:187-193 (1993). Further examples may be found in Sambrook and Russel, 2001. Molecular Cloning, A Laboratory Manual. Third Edition. Cold Spring Harbor laboratory, Cold Spring Harbor Press, NY, herein incorporated by reference.

Alternatively, a cassette encoding a single restriction enzyme recognition sites for the insertion of DNA encoding an ATG translational start site and an Smt3 fragment may be inserted into a cloning vector as described above and the vector may then be topoisomerase adapted to insert a nucleic acid encoding a poly amino acid of interest. Other topoisomerase cloning vectors are available from Invitrogen Corp., Carlsbad, Calif., which provides detailed descriptions of topoisomerase cloning systems.

The Ulp1 protease fragment from residues 403-621 has remarkable properties. It has a cleavage specificity identical to native full length Ulp1, but is much more active. For instance, cleavage of a Smt3-GST fusion by Ulp1(403-621) occurs rapidly and specifically even at 4° C. under normal conditions of buffer pH and ionic strength, where cleavage by other site-specific proteases would be so slow as to be almost negligible except after extended periods such as overnight, when non-specific cleavage becomes evident. Normal conditions for cleavage reactions with 1.0 mg/ml substrate and $10^{-3}$ to $10^{-4}$ mg/ml $Ulp1(403-621)_p$ are performed in 150 mM NaCl, 1 mM DTT, 10 mM Tris-HCl pH 8.0 at 30° C. Alternatively, cleavage may be achieved by reaction in lysis buffer: 330 mM Tris-HCl pH 8.0, 75 mM EDTA, 1 mM PMSF, 2 mM dithiothreitol (DTT) for 3 hours at 37° C.

C-terminally His-tagged Smt3(13-101) was expressed from pET-28b and was purified as $Ulp1(403-621)_p$. Smt3-GFPuv was constructed by ligating SMT3 into pGFPuv (Clonetech, Palo Alto, Calif.), overexpressed in JM109 E. coli cells, purified by standard chromatographic techniques and detected using fluorescence. Sumo-p-His was prepared as Smt3(13-101)p. $His_6$-ubiquitin-Smt3-HA was expressed from QE30 (Li and Hochstrasser, 1999, Nature 398:246-251) in JM109 E. coli cells and purified by Ni affinity and standard chromatographic techniques.

A recombinant Smt3-GST fusion protein with a thrombin sensitive cleavage site is cleaved more slowly than the Ulp1-sensitive site cleaved by Ulp1(403-621), even at room temperature overnight leaving an incomplete digest. Further incubation leads to non-specific digestion. By contrast, the protease fragment Ulp1(residues 403-621) cleaves completely and specifically in one hour under identical conditions of concentration of enzyme and substrate, with no detectable non-specific cleavage as judged by SDS-PAGE analysis. Similar specificity of cleavage may be achieved with other proteases, such as the tobacco etch virus (TEV) protease, but the cleavage reaction rate is very slow when compared to that of Ulp1 and more especially when compared with Ulp1(403-621).

EXAMPLES

The Smt3 fusion cassette has been constructed by PCR to mutate 3' nucleotides to accommodate a 3' BamHI restriction site to minimize the number of amino acids between the Ulp1(403)$_p$ cleavage site and the respective fusion partner. The construct was made by PCR using *S. cerevisiae* genomic DNA as template. Two primers, a 5' primer (SEQ. ID. NO: 5) and a 3' primer (SEQ. ID. NO: 7) were constructed to facilitate cloning of the Smt3 cassette into pET28b (Novagen, Madison, Wis.). The nucleotide sequences of these 5' and 3' primers are as follows:

```
              NheI
              SITE
              -------
5' primer:  GCG GCT AGC ATG TCG GAC TCA GAA GTC AAT
                        M   S   D   S   E   V   N

CAA G
            Q
```

The Smt3 encoded amino acids (SEQ. ID. NO: 6) are denoted in upper case letters in the single letter amino acid code below the codons specifying each amino acid.

```
            BamHI
            SITE
            -------
3' primer:  GCG GGA TCC ACC AAT CTG TTC TCT GTG AGC
                 s   g   G   I   Q   E   R   H   A

CTC A
            E
```

The Smt3 reverse complement encoded amino acids (SEQ. ID. NO: 8) are denoted in upper case letters. The serine reside that is altered in the primer is denoted in lower case lettering.

The native C-terminal codons (SEQ. ID. NO: 9) and residues (SEQ. ID. NO: 10) for Smt3 as they occur in nature are as follows:

```
3'  CTA ATA CGT AGC ACC ACC AAT CTG TTC TCT GTG AGC
     *   Y   T   A   G   G   I   Q   E   R   H   A

CTC A . . .
    E
```

The one letter amino acid code is shown below the anticodon of the reverse (anti-sense) primer. The asterisk denotes the reverse complement of the translation terminator sequence, TAG corresponding to UAG in the messenger RNA sequence transcribed from the native Smt3 gene.

By primer extension on yeast (*S. cerevisiae*) genomic DNA template and further polymerase chain reaction (PCR) amplification, the ACC glycine codon was mutated to TCC to generate a BamHI sequence that overlaps the Ulp1 cleavage site.

The PCR product was cleaved with NheI and BamHI and cloned into these respective sites of pET28b, creating an N-terminal thrombin cleavable hexahistidine tagged Smt3 fusion protein. The nucleic acid encoding the polyamino acid or gene of interest can then be cloned into the BamHI site and any other downstream site in the multiple cloning site region of the vector, in this case pET28b. This plasmid, pSUMO was deposited on Mar. 29, 2005 with the American Type Culture Collection, 10801 University Blvd., Manassas, Va. 20110 under the terms of the Budapest Treaty and assigned patent deposit designation no. PTA-6647.

Example 1

Expression, Cleavage and HPLC Purification of a 14 mer Peptide Derived from the Sequence for Human IκBα

Figure 1B:
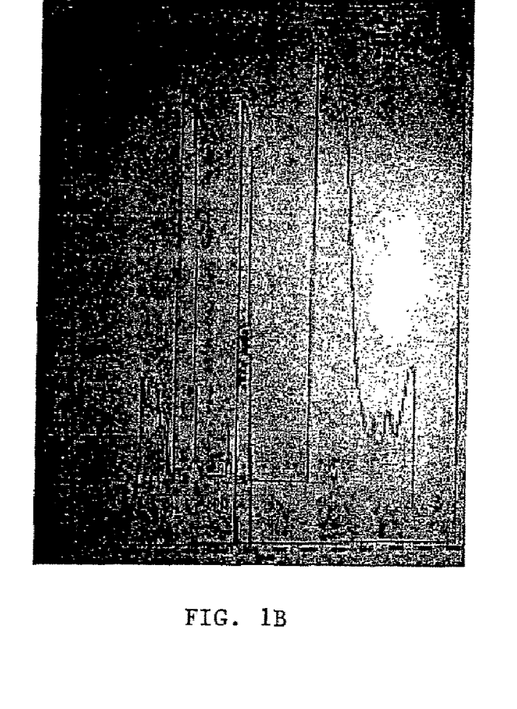
FIG. 1B. High Performance Liquid Chromatography (HPLC) Trace.
Figure 2:
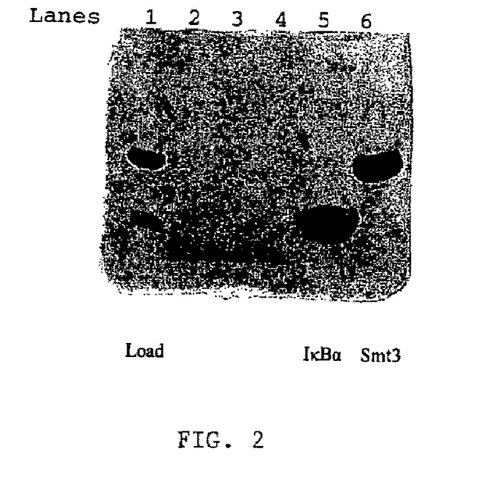
FIG. 2. SDS-polyacrylamide Gel Electrophoresis (SDS-PAGE) Analysis of the HPLC Purification of the Smt3-IκBα Fusion.

The coding region for the IκBα peptide was designed by engineering complementary PCR oligonucleotides that code for an N-terminal BamHI site, the 14 amino acids contained in the coding region for IκBα, and a stop codon followed by a HindIII restriction enzyme site. The complementary primers were annealed, digested with respective restriction enzymes, gel purified, and ligated into a vector containing a hexahistidine tagged Smt3 coding region. An expression strain of *E. coli* was transformed with the resulting plasmid, grown, and the culture was induced for protein expression. The Smt3-IκBα recombinant fusion protein was isolated from the bacterial lysate by Ni-affinity chromatography and sized by gel filtration. The resulting peak was cleaved using a 1:1000 by mass ratio of Ulp1 to Smt3 fusion. After 2 hours, the mixture was purified by C18 reverse phase HPLC (FIG. 1B), and peaks were analyzed by SDS-PAGE (See FIG. 2).

Example 2

Figure 3:
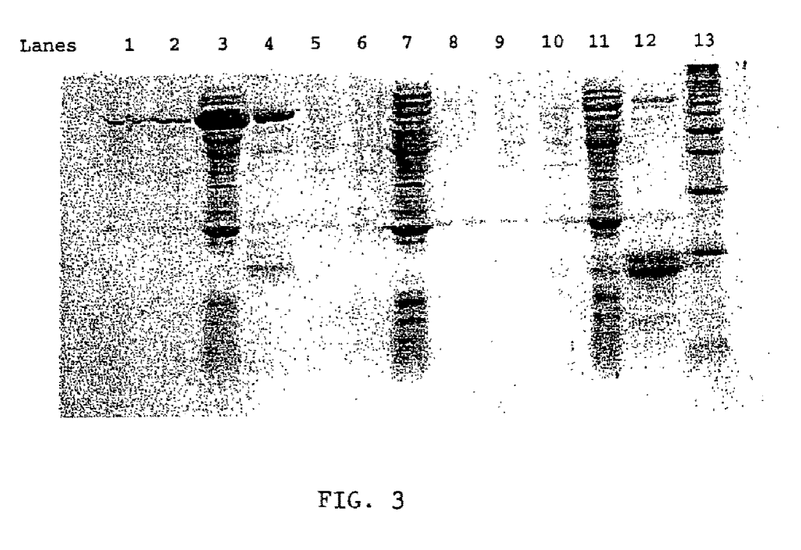
FIG. 3. SDS-PAGE Analysis Expression Products of *E. coli* and *S. cerevisiae* Phosphatidylserine Synthase (PSS).

Expression, Purification of the Membrane-Associated Phosphatidylserine Synthase (PSS) Enzymes Genes were cloned from *E. coli* and *S. cerevisiae*, expressed and purified in *E. coli* (FIG. 3). The C-terminal histidine tagged *E. coli* phosphatidylserine synthase (PSS) construct was not sufficiently expressed to allow visualization on Coomassie blue stained SDS gels or in amounts sufficient for purification by Ni-column affinity chromatography. Without being bound by any particular theory, the inventor believes that membrane proteins are generally very difficult to express and purify from bacterial expression systems. By contrast the fusion with the expression enhancing amino acid sequence of the recombinant fusion proteins of the present invention increases both expression and solubility of the recombinant protein. This is shown for example by comparison of the properties of the *S. cerevisiae* PSS enzyme, and the *S. cerevisiae* PSS enzyme of the fusion protein. The N-terminal Smt3 tag to the *S. cerevisiae* PSS enzyme of the fusion protein enhances the expression properties of this enzyme.

Example 3

Figure 4:
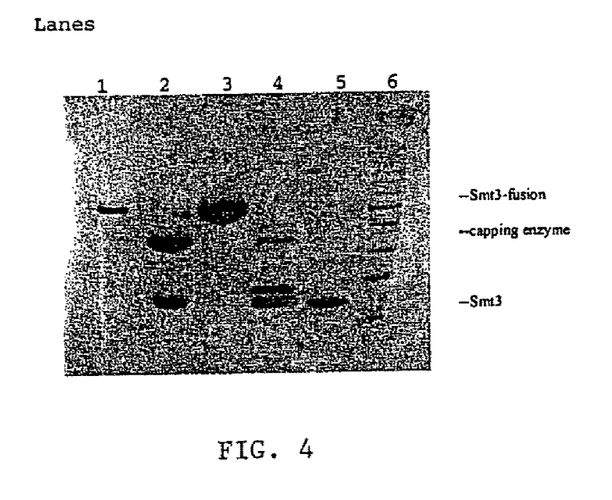
FIG. 4. Purified Fractions of the *S. cerevisiae* mRNA Triphosphatase Analyzed by SDS-PAGE.
Figure 5:
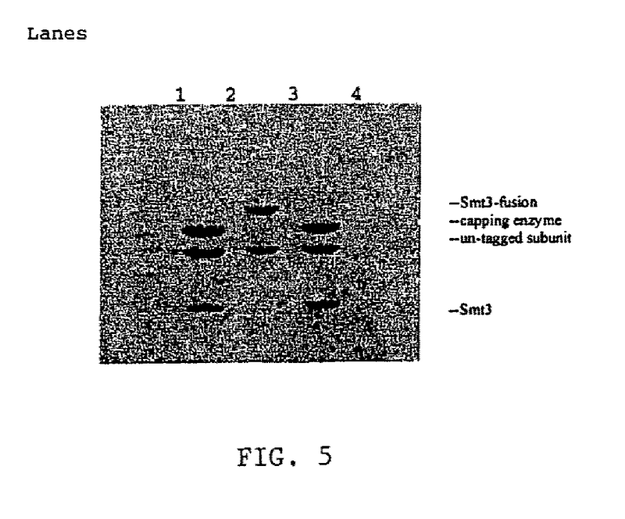
FIG. 5. Purified Fractions of the *C. albicans* Capping Enzyme Analyzed by SDS-PAGE.

Expression, Purification, and Cleavage of Protease-Sensitive mRNA Capping Proteins with the Smt3 Fusion System This example demonstrates the protease specificity exhibited by the Ulp1 protease by showing that no degradation of the protease-sensitive mRNA capping proteins was detected. The mRNA capping enzymes from *S. cerevisiae* (FIG. 4) and *C. albicans* (FIG. 5) are very sensitive to proteolytic degradation if exposed to thrombin, factor Xa, or PRECISSION™ protease (Pharmacia, Kalamazoo, Mich.). Several capping enzyme constructs were prepared using the Smt3 fusion system to obtain material with precise cleavage sites posterior to the Ulp1 cleavage sequence. Enzymes were purified using Ni-affinity chromatography. Cleavage of the Smt3-fusions was achieved in a 1-2 hour reaction containing a 1:1000 by mass ratio of protease to fusion protein as described above.

Example 4

Smt3-Fusion with Full-Length Human IκBα

Figure 6:
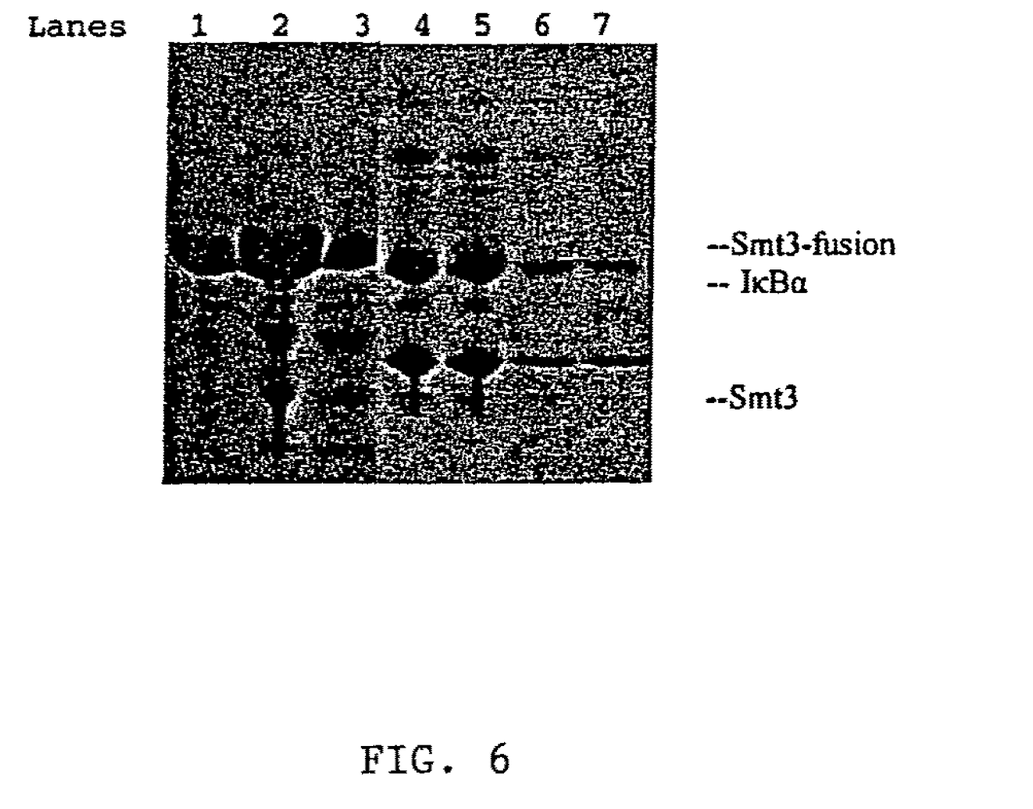
FIG. 6. Purified Fractions of the IκBα Protein Before and after Ulp1 Cleavage Analyzed by SDS-PAGE.

Expression, purification, and cleavage of full-length human IκBα was achieved using the Smt3-fusion system (FIG. 6).

The coding sequence for full length IκBα (GenBank accession M69043) was amplified from a human cDNA library using 2 primers, a 5' primer that encoded BamHI restriction enzyme sequence and the DNA sequence for IκBα that encoded residues 1 to 7, and a 3' primer that encoded IκBα residues 478 to 485, a stop codon, and a sequence that encoded a HindIII restriction enzyme site. The PCR product was sub-cloned into the vector containing the Smt3 fusion sequence. The resulting construct was used to over-express the polyhistidine tagged Smt3-IκBα recombinant fusion protein in E. coli. The resulting recombinant fusion protein was purified from E. coli lysates and purified using Ni-affinity chromatography, and cleaved with the Ulp1 protease.

Other laboratories have reported difficulties, including the expression of insoluble IκBα in recombinant expression systems. Here efficient expression was achieved by expressing the IκBα as part of a fusion molecule with Smt3. This approach alleviated the expression problem and enabled large amounts of the soluble protein to be purified from the Smt3-fusion system. Further materials and methods useful in practicing the present invention are described "Ulp1-SUMO Crystal Structure and Genetic Analysis Reveal Conserved Interactions and a Regulatory Element Essential for Cell Growth in Yeast." and in Li & Hochstrasser, 1999, Nature 398:246-251.

Those of skill in the art will immediately recognize the full scope of this invention as contemplated and its equivalents which are encompassed by the specification herein and claims appended hereto.

Incorporation of Sequence Listing

Incorporated herein by reference in its entirety is the Sequence Listing for the application. The Sequence Listing is disclosed on a computer-readable ASCII text file titled, "sequence_listing.txt", created on Oct. 10, 2008. The sequence_listing.txt file is 3.42 kb in size.

We claim:

1. A method of expressing a recombinant poly-amino acid of interest, the method comprising:
    i) providing a vector encoding a fusion protein, said fusion protein comprising the recombinant poly-amino acid of interest and a small ubiquitin-like molecule (SUMO) cleavable by an active fragment of Ulp1 protease comprising amino acid residues 403-621 of yeast Ulp1, wherein the poly-amino acid of interest is expressed at 1% or less than 1% of total protein by weight or is expressed defectively when it does not contain the expression enhancing amino acid sequence in a recombinant expression system; and
    ii) expressing the fusion protein from the vector.

2. The method of claim 1, further comprising cleaving the fusion protein with a protease to release the recombinant poly-amino acid of interest.

3. The method of claim 2, wherein said protease is Ulp1.

4. The method of claim 3, wherein the protease comprises amino acid residues 403-621 of yeast Ulp1.

5. The method of claim 2, wherein the released poly-amino acid of interest has an N-terminal serine.

6. The method of claim 1, wherein said fusion protein is expressed in a recombinant host cell.

7. The method of claim 1, wherein the SUMO is Smt3.

8. The method of claim 7, wherein the Smt3 is identified in SEQ ID NO:3.

9. The method of claim 1, wherein the SUMO comprises amino acid residues 1-98 of SEQ ID NO: 3.

10. The method of claim 1, wherein the SUMO comprises amino acid residues 13-101 of SEQ ID NO: 3.

11. The method of claim 1, wherein the SUMO comprises amino acid residues 14-98 of SEQ ID NO: 3.

12. The method of claim 1, wherein said vector comprises plasmid ATCC PTA-6647.

13. The method of claim 1, wherein the poly-amino acid of interest is an immunoglobulin, a membrane associated protein, a protein or peptide that precipitates in recombinant host cells, or a protein produced in a non-native or inactive form.

14. The method of claim 1, wherein said fusion protein further comprises a purification tag.

15. The method of claim 2, further comprising purifying the recombinant poly-amino acid of interest.

16. The method of claim 15, wherein the purified recombinant poly-amino acid of interest has an N-terminal serine.

17. The method of claim 1, wherein the recombinant poly-amino acid of interest is located C-terminally to a purification tag and wherein the purification tag and the recombinant poly-amino acid of interest are separated by the expression enhancing amino acid sequence.

18. A method of expressing a recombinant poly-amino acid of interest, the method comprising:
    i) providing a vector encoding a fusion protein, said fusion protein comprising the recombinant poly-amino acid of interest and a small ubiquitin-like molecule (SUMO) cleavable by an active fragment of Ulp1 protease comprising amino acid residues 403-621 of yeast Ulp1, wherein the poly-amino acid of interest is expressed at 1% or less than 1% of total protein by weight or is expressed defectively when it does not contain the expression enhancing amino acid sequence in a recombinant expression system;
    ii) expressing the fusion protein from the vector;
    iii) purifying the fusion protein;
    iv) cleaving the fusion protein with a protease to release the poly-amino acid of interest; and
    v) purifying the recombinant poly-amino acid of interest.

19. The method of claim 18, wherein the fusion protein is purified by means of a purification tag.

20. The method of claim 18, wherein the released poly-amino acid of interest has an N-terminal serine.

21. The method of claim 18, wherein said protease is Ulp1.

22. The method of claim 18, wherein the protease comprises amino acid residues 403-621 of yeast Ulp1.

23. The method of claim 18, wherein the SUMO is Smt3.

24. A kit comprising a recombinant vector encoding a small ubiquitin-like molecule (SUMO) cleaveable by an active fragment of Ulp1 protease comprising amino acid residues 403-621 of yeast Ulp1, and a cloning site suitable for cloning a nucleic acid sequence encoding a poly-amino acid of interest,
    wherein the poly-amino acid of interest is expressed at 1% or less than 1% of total protein by weight or is expressed defectively when it does not contain the small ubiquitin-like molecule (SUMO) that functions as an expression enhancing amino acid sequence in a recombinant expression system.

25. The kit of claim 24, wherein the vector further encodes a purification tag.

26. The kit of claim 24, wherein the poly-amino acid of interest has an N-terminal serine when released.

27. The kit of claim 24, further comprising a protease for cleaving the poly-amino acid of interest from the fusion protein, said fusion protein comprising the poly-amino acid of interest and the SUMO.

28. The kit of claim 27, wherein said protease is Ulp1.

29. The kit of claim 28, wherein the protease comprises amino acid residues 403-621 of yeast Ulp1.

30. The kit of claim 24, wherein the SUMO is Smt3.

31. The kit of claim 24, wherein said cloning site is a multiple cloning site.

* * * * *

SEQUENCE LISTING

```
<160> NUMBER OF SEQ ID NOS: 10

<210> SEQ ID NO 1
<211> LENGTH: 10
<212> TYPE: PRT
<213> ORGANISM: Artificial Sequence
<220> FEATURE:
<223> OTHER INFORMATION: His tag

<400> SEQUENCE: 1

His His His His His His His His His His
1               5                   10

<210> SEQ ID NO 2
<211> LENGTH: 306
<212> TYPE: DNA
<213> ORGANISM: Saccharomyces cerevisiae

<400> SEQUENCE: 2
atgtcggact cagaagtcaa tcaagaagct aagccagagg tcaagccaga agtcaagcct        60
gagactcaca tcaatttaaa ggtgtccgat ggatcttcag agatcttctt caagatcaaa       120
aagaccactc ctttaagaag gctgatggaa gcgttcgcta aaagacaggg taaggaaatg       180
gactccttaa gattcttgta cgacggtatt agaattcaag ctgatcagac ccctgaagat       240
ttggacatgg aggataacga tattattgag gctcacagag aacagattgg tggtgctacg       300
tattag                                                                 306

<210> SEQ ID NO 3
<211> LENGTH: 101
<212> TYPE: PRT
<213> ORGANISM: Saccharomyces cerevisiae

<400> SEQUENCE: 3

Met Ser Asp Ser Glu Val Asn Gln Glu Ala Lys Pro Glu Val Lys Pro
1               5                   10                  15

Glu Val Lys Pro Glu Thr His Ile Asn Leu Lys Val Ser Asp Gly Ser
            20                  25                  30
```

```
Ser Glu Ile Phe Phe Lys Ile Lys Lys Thr Thr Pro Leu Arg Arg Leu
         35                  40                  45

Met Glu Ala Phe Ala Lys Arg Gln Gly Lys Glu Met Asp Ser Leu Arg
 50                  55                  60

Phe Leu Tyr Asp Gly Ile Arg Ile Gln Ala Asp Gln Thr Pro Glu Asp
 65                  70                  75                  80

Leu Asp Met Glu Asp Asn Asp Ile Ile Glu Ala His Arg Glu Gln Ile
             85                  90                  95

Gly Gly Ala Thr Tyr
            100

<210> SEQ ID NO 4
<211> LENGTH: 8
<212> TYPE: PRT
<213> ORGANISM: Artificial Sequence
<220> FEATURE:
<223> OTHER INFORMATION: Antibody binding peptide

<400> SEQUENCE: 4

Asp Tyr Lys Asp Asp Asp Asp Lys
1               5

<210> SEQ ID NO 5
<211> LENGTH: 34
<212> TYPE: DNA
<213> ORGANISM: Artificial Sequence
<220> FEATURE:
<223> OTHER INFORMATION: 5' primer for cloning of the Smt3 cassette

<400> SEQUENCE: 5
gcggctagca tgtcggactc agaagtcaat caag                              34

<210> SEQ ID NO 6
<211> LENGTH: 8
<212> TYPE: PRT
<213> ORGANISM: Saccharomyces cerevisiae

<400> SEQUENCE: 6

Met Ser Asp Ser Glu Val Asn Gln
1               5

<210> SEQ ID NO 7
<211> LENGTH: 34
<212> TYPE: DNA
<213> ORGANISM: Artificial Sequence
<220> FEATURE:
<223> OTHER INFORMATION: 3' primer for cloning of the Smt3 cassette

<400> SEQUENCE: 7
actccgagtg tctcttgtct aaccacctag ggcg                              34

<210> SEQ ID NO 8
<211> LENGTH: 10
<212> TYPE: PRT
<213> ORGANISM: Saccharomyces cerevisiae

<400> SEQUENCE: 8

Glu Ala His Arg Glu Gln Ile Gly Gly Ser
1               5                   10

<210> SEQ ID NO 9
<211> LENGTH: 40
<212> TYPE: DNA
<213> ORGANISM: Saccharomyces cerevisiae
```

-continued

```
<400> SEQUENCE: 9
actccgagtg tctcttgtct aaccaccacg atgcataatc                    40

<210> SEQ ID NO 10
<211> LENGTH: 12
<212> TYPE: PRT
<213> ORGANISM: Saccharomyces cerevisiae

<400> SEQUENCE: 10

Glu Ala His Arg Glu Gln Ile Gly Gly Ala Thr Tyr
1               5                   10
```